(12) United States Patent
Liu et al.

(10) Patent No.: US 11,759,654 B2
(45) Date of Patent: Sep. 19, 2023

(54) RADIOTHERAPY DEVICE AND CONTROL DRIVING METHOD THEREOF

(71) Applicant: OUR UNITED CORPORATION, Xi'an (CN)

(72) Inventors: Haifeng Liu, Xi'an (CN); Daliang Li, Xi'an (CN)

(73) Assignee: OUR UNITED CORPORATION, Xi'an (CN)

( * ) Notice: Subject to any disclaimer, the term of this patent is extended or adjusted under 35 U.S.C. 154(b) by 0 days.

(21) Appl. No.: 18/068,063

(22) Filed: Dec. 19, 2022

(65) Prior Publication Data

US 2023/0117277 A1 Apr. 20, 2023

Related U.S. Application Data

(63) Continuation of application No. 17/183,459, filed on Feb. 24, 2021, now abandoned, and a continuation of application No. PCT/CN2019/092506, filed on Jun. 24, 2019.

(30) Foreign Application Priority Data

Aug. 24, 2018 (CN) .......................... 201810977446.8

(51) Int. Cl.
*A61N 5/10* (2006.01)

(52) U.S. Cl.
CPC .......... *A61N 5/1042* (2013.01); *A61N 5/1001* (2013.01); *A61N 5/1065* (2013.01); *A61N 2005/1019* (2013.01); *A61N 2005/1094* (2013.01)

(58) Field of Classification Search
CPC .. A61N 5/1042; A61N 5/1001; A61N 5/1065; A61N 2005/1019; A61N 2005/1094; A61N 2005/1052; A61N 2005/1055; A61N 2005/1058; A61N 2005/1061; A61N 5/1049; A61N 5/1067;
(Continued)

(56) References Cited

U.S. PATENT DOCUMENTS

| | | |
|---|---|---|
| 5,448,611 A | 9/1995 | Kerjean |
| 5,537,452 A | 7/1996 | Shepherd et al. |
| 6,438,203 B1 | 8/2002 | Shipeng et al. |

(Continued)

FOREIGN PATENT DOCUMENTS

| | | |
|---|---|---|
| CN | 2258407 Y | 7/1997 |
| CN | 1275410 A | 12/2000 |

(Continued)

*Primary Examiner* — Marcus H Taningco
(74) *Attorney, Agent, or Firm* — Emerson, Thomson & Bennett, LLC; Roger D. Emerson

(57) ABSTRACT

A radiotherapy device and a control driving method thereof are provided. The radiotherapy device includes a radiation source apparatus having a plurality of radiation sources, a source carrier and a collimator. The source carrier includes a source box and a source box region conforming to a shape of the source box, the source box is detachably fixed at the source box region, the plurality of radiation sources are mounted in the source box, the source box is provided with a first connecting part, the source carrier is provided with a second connecting part, and the first connecting part is configured to connect the second connecting part.

20 Claims, 11 Drawing Sheets

(58) Field of Classification Search
CPC .............. A61N 5/1084; A61N 5/103; A61N 2005/1054; A61N 2005/1092
See application file for complete search history.

(56) References Cited

U.S. PATENT DOCUMENTS

| | | | |
|---|---|---|---|
| 8,641,592 | B2 | 2/2014 | Yu |
| 9,555,264 | B1 | 1/2017 | Sahadevan |
| 2005/0276377 | A1 | 12/2005 | Carol |
| 2008/0253516 | A1 | 10/2008 | Hui et al. |
| 2015/0202465 | A1 | 7/2015 | Zhao |
| 2017/0065834 | A1 | 3/2017 | Liu |
| 2019/0001146 | A1* | 1/2019 | Liu .................... A61N 5/01 |
| 2020/0238106 | A1 | 7/2020 | Xiao et al. |

FOREIGN PATENT DOCUMENTS

| | | | | |
|---|---|---|---|---|
| CN | 101195058 | A | 6/2008 | |
| CN | 101195058 | B | 5/2010 | |
| CN | 101961530 | A | 2/2011 | |
| CN | 102430206 | A | 5/2012 | |
| CN | 203647890 | U * | 6/2014 | .............. A61N 5/06 |
| CN | 104837523 | A | 8/2015 | |
| CN | 109011217 | A | 12/2018 | |
| CN | 109011218 | A | 12/2018 | |
| CN | 109011219 | A | 12/2018 | |
| CN | 109157761 | A | 1/2019 | |
| CN | 109157762 | A | 1/2019 | |
| EP | 1057499 | A | 12/2000 | |
| EP | 1917911 | A | 5/2008 | |
| JP | 2003205042 | A | 7/2003 | |
| JP | 2011007733 | A | 1/2011 | |
| SE | 517625 | C2 | 6/2002 | |
| WO | WO2008106468 | A1 | 9/2008 | |
| WO | WO2015150796 | A1 | 10/2015 | |
| WO | WO2017020244 | A1 | 2/2017 | |
| WO | WO-2018176473 | A1 * | 10/2018 | .............. A61N 5/10 |

\* cited by examiner

RADIOTHERAPY DEVICE AND CONTROL DRIVING METHOD THEREOF

CROSS-REFERENCE TO RELATED APPLICATIONS

The present disclosure is a continuation of U.S. application Ser. No. 17/183,459, filed on Feb. 24, 2021, entitled "RADIOTHERAPY DEVICE AND CONTROL DRIVING METHOD THEREOF", which is a continuation of international application PCT/CN2019/092506 filed on Jun. 24, 2019, entitled "RADIOTHERAPY APPARATUS, CONTROLLING AND DRIVING METHOD AND APPARATUS, AND SYSTEM", which claims priority to Chinese Patent Application No. 201810977446.8 filed on Aug. 24, 2018, entitled "RADIOTHERAPY DEVICE AND CONTROL DRIVING METHOD THEREOF", the entire contents of which are incorporated herein by reference.

TECHNICAL FIELD

The present disclosure relates to the field of medical technologies, and in particular to, a radiotherapy device, a control driving method, a control driving device, and a control driving system.

BACKGROUND

With the development of medical technologies, radiotherapy is increasingly widely used in the treatment of tumors.

A radiotherapy device configured to treat a head tumor in related technologies mainly includes a radiation source apparatus and a treatment couch. The arrangement of radiation sources in the radiation source apparatus is shown in FIG. 1. Radiation sources 111 are divided into six groups, and are distributed on a source carrier 11. Referring to FIG. 2, a collimator 12 is provided with a plurality of collimating channels, and rays emitted from the radiation sources pass through the collimating channels and intersect at a focus. The treatment couch is configured to carry a patient and move the patient to the inside of a treatment chamber of the radiation source apparatus, such that a nidus of the patient is located at the focus for radiotherapy.

SUMMARY

The present disclosure provides a radiotherapy device, a control driving method, a control driving device, and a control driving system.

An embodiment of the present disclosure provides a radiotherapy device, including a radiation source apparatus, where the radiation source apparatus includes a plurality of radiation sources and a collimator, source points of the plurality of radiation sources are within a preset included angle range in a longitude direction, and the preset included angle range is 5 to 60 degrees. The collimator is provided with a plurality of collimating hole groups, and an included angle of each of the collimating hole groups in the longitude direction is within the preset included angle range; and each of the collimating hole groups includes a plurality of collimating holes, and radiation beams emitted from the plurality of radiation sources intersect at a common focus after passing through the collimating holes of the collimating hole groups.

An embodiment of the present disclosure further provides a control driving method for a radiotherapy device, the radiotherapy device includes a plurality of radiation sources, and source points of the plurality of radiation sources are within a preset included angle range in a longitude direction. The method includes:

acquiring at least one beam emission angle range; and driving the radiotherapy device to emit radiation beams in the beam emission angle range, the radiation beams intersecting at a common focus.

An embodiment of the present disclosure further provides a control driving device for a radiotherapy device, including: a processor configured to implement the control driving method provided in the present disclosure.

An embodiment of the present disclosure further provides a radiotherapy system, including: the radiotherapy device provided in the present disclosure, and the control driving device provided in the present disclosure.

An embodiment of the present disclosure further provides a radiotherapy device. The radiotherapy device includes a radiation source apparatus having a plurality of radiation sources, a source carrier and a collimator. Source points of the plurality of radiation sources are within a preset included angle range in a longitude direction. The collimator is provided with a plurality of collimating hole groups, and an included angle of each of the collimating hole groups in the longitude direction is within the preset included angle range between 5 to 60 degrees. Each of the collimating hole groups includes a plurality of collimating holes, and radiation beams emitted from the plurality of radiation sources intersect at a common focus after passing through the collimating holes of the collimating hole groups. The source carrier comprises a source box and a source box region conforming to a shape of the source box, the source box is detachably fixed at the source box region, the plurality of radiation sources are mounted in the source box, the source box is provided with a first connecting part, the source carrier is provided with a second connecting part, and the first connecting part is configured to connect the second connecting part.

DETAILED DESCRIPTION

In order to make the principles, technical solutions, and advantages of the present disclosure clearer, embodiments of the present disclosure will be further described in detail below with reference to the accompanying drawings.

Figure 1:
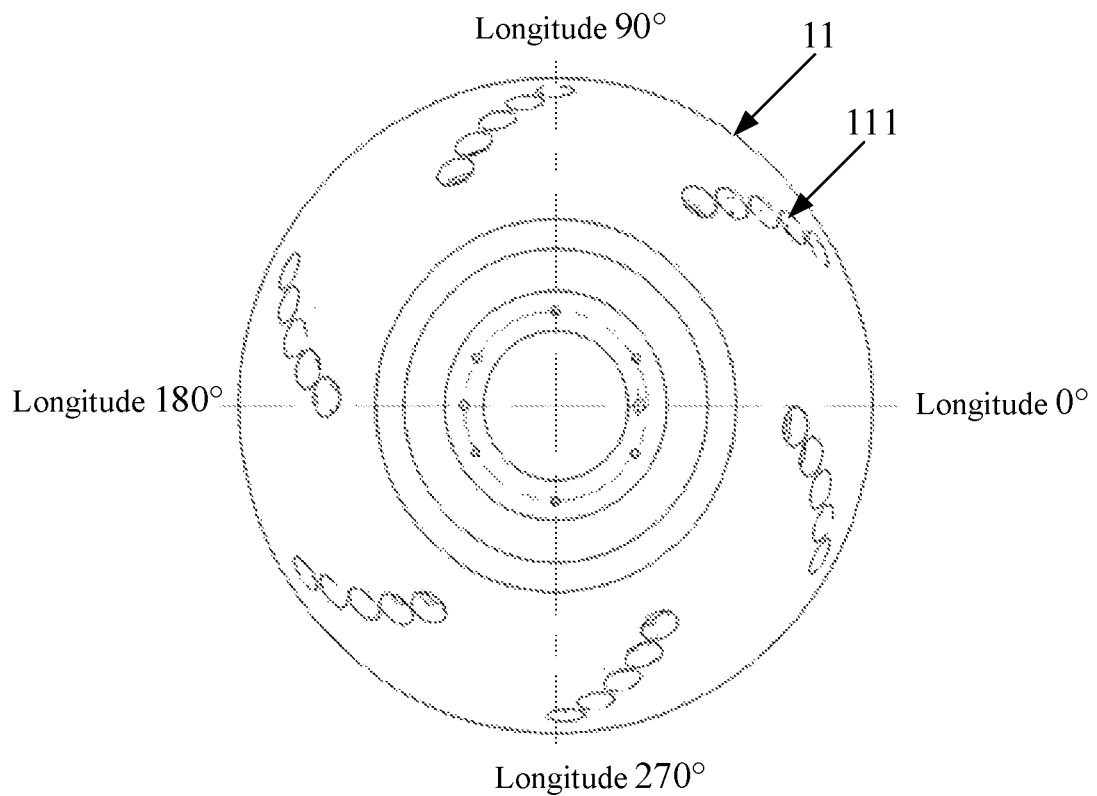
FIG. 1 is a schematic structural diagram of a top view of a source carrier in a related technology provided in an embodiment of the present disclosure.
Figure 2:
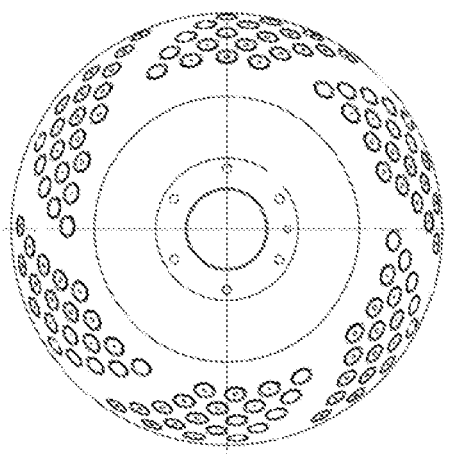
FIG. 2 is a schematic structural diagram of a top view of a collimator in a related technology provided in an embodiment of the present disclosure.

A source carrier of a radiotherapy device in related technologies is bowl-shaped, as shown in FIG. 1. Radiation sources 111 are divided into six groups, and there are five radiation sources in each group, totaling 30 radiation sources, which are distributed on a source carrier 11. A collimator 12 is shown in FIG. 2, six collimating channel groups are provided on the collimator 12, and the six collimating channel groups correspond to positions of the radiation sources in the six groups. Each collimating channel group includes four subgroups, where collimating holes in one of the subgroups are filled with solid tungsten rods to realize closed source shielding, each of the other subgroups includes 5 collimating holes, and the collimating holes in different subgroups are of different sizes.

During treatment, the source carrier 11 and the collimator 12 may be driven to rotate mutually, to switch between different sizes of collimating holes and realize switching on/off the radiation sources by shielding the radiation sources through the collimator, but the switching between different sizes of the collimating holes in the six groups and the switching on/off the radiation sources are implemented simultaneously, and one group thereof cannot be controlled individually. Therefore, during treatment, the only way to avoid eyes (sensitive tissues and organs) is to adjust a gamma angle, such that rays avoid the eyes.

The present disclosure provides a radiotherapy device, including a radiation source apparatus. The radiation source apparatus includes a plurality of radiation sources and a collimator. Source points of the plurality of radiation sources are within a preset included angle range in a longitude direction. The collimator is provided with a plurality of collimating hole groups, an included angle of each of the collimating hole groups in the longitude direction is within the preset included angle range; each of the collimating hole groups includes a plurality of collimating holes, and radiation beams emitted from the plurality of radiation sources intersect at a common focus after passing through the collimating holes of the collimating hole groups.

Figure 5:
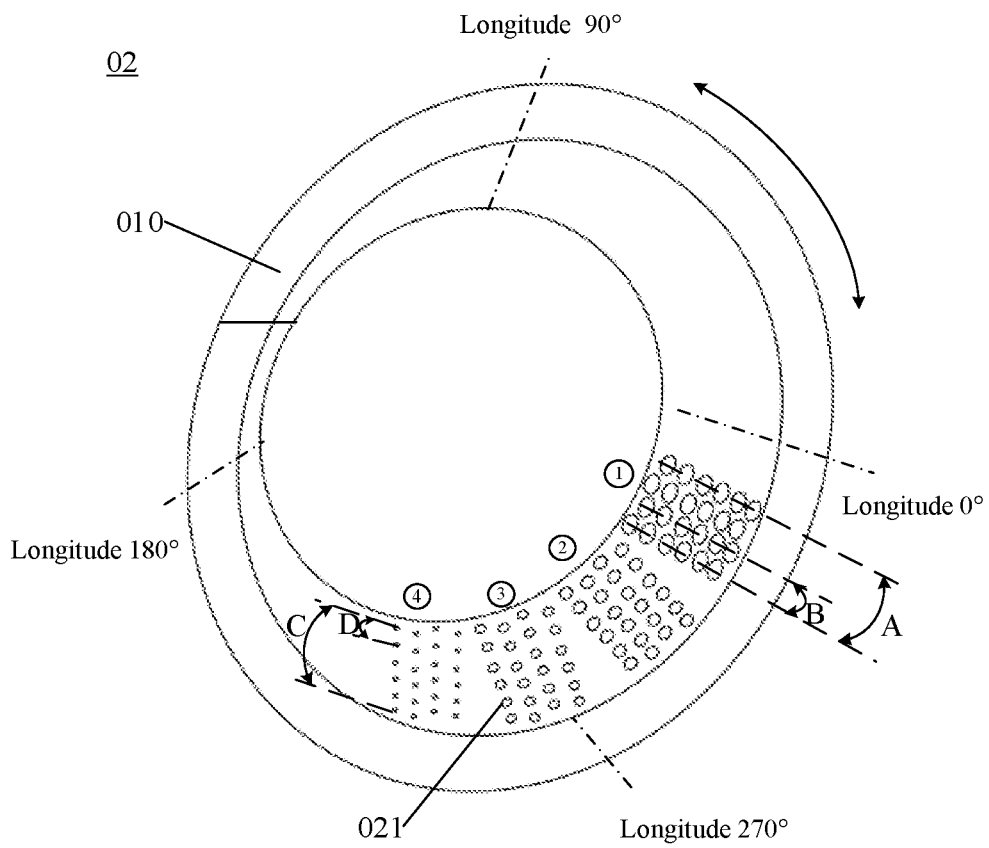
FIG. 5 is a schematic diagram of a collimator provided in an embodiment of the present disclosure.

It should be noted that in the present disclosure, the radiation source may be an X-ray accelerating system, and then the radiation beam may be an X-ray beam; or the radiation source may be a γ-radioactive source (hereinafter also referred to as the radiation source), and then the radiation beam may be a γ-ray beam. If the radiation beam is the X-ray beam, and the principle of generating the X-ray beam is that an electron beam hits a target body to generate the X-ray beam, then a source point of the radiation source may be an intersection point of reverse extension lines of X-ray beams 07 as shown in FIG. 5 (i.e., a source point 06 in FIG. 3). If the radiation beam is the γ-ray beam, then the source point of the radiation source may be an isotope radiation source, e.g., cobalt-60.

The radiation source being the X-ray accelerating system and the γ-radioactive source will be described respectively below.

Figure 9:
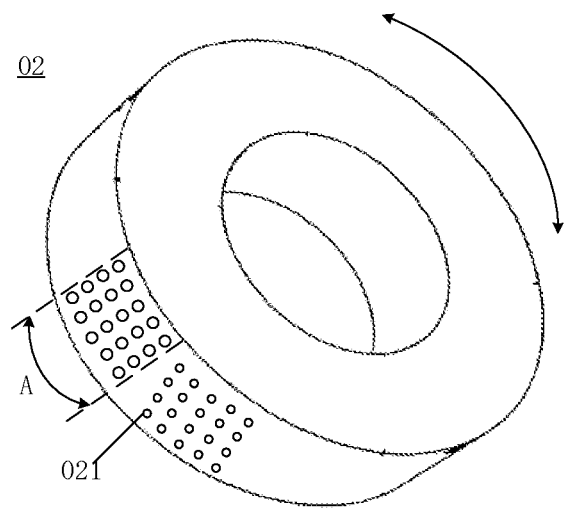
FIG. 9 is a schematic diagram of another collimator provided in an embodiment of the present disclosure.
Figure 10:
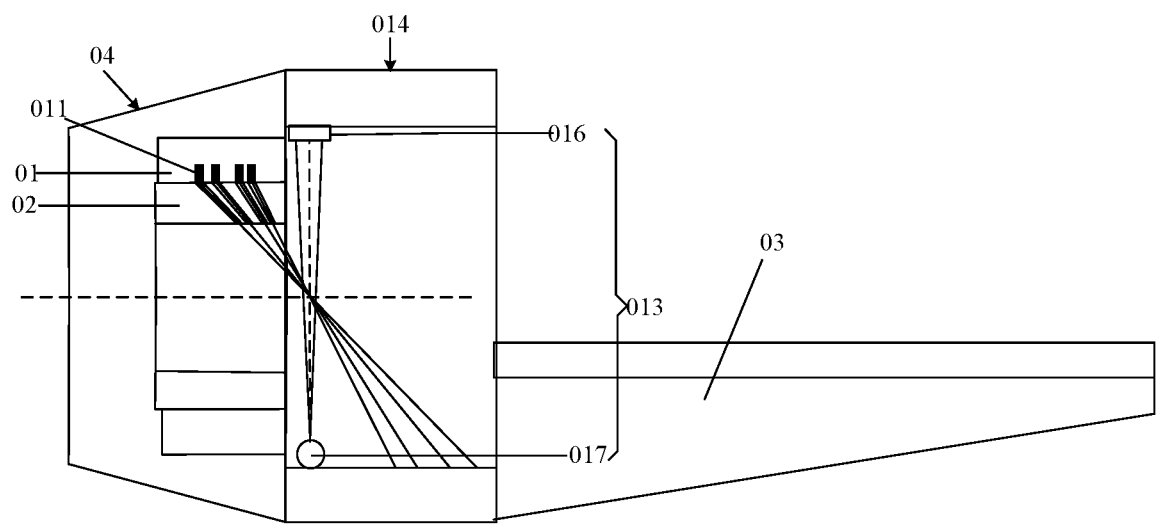
FIG. 10 is a schematic diagram of still another radiotherapy device provided in an embodiment of the present disclosure.
Figure 11:
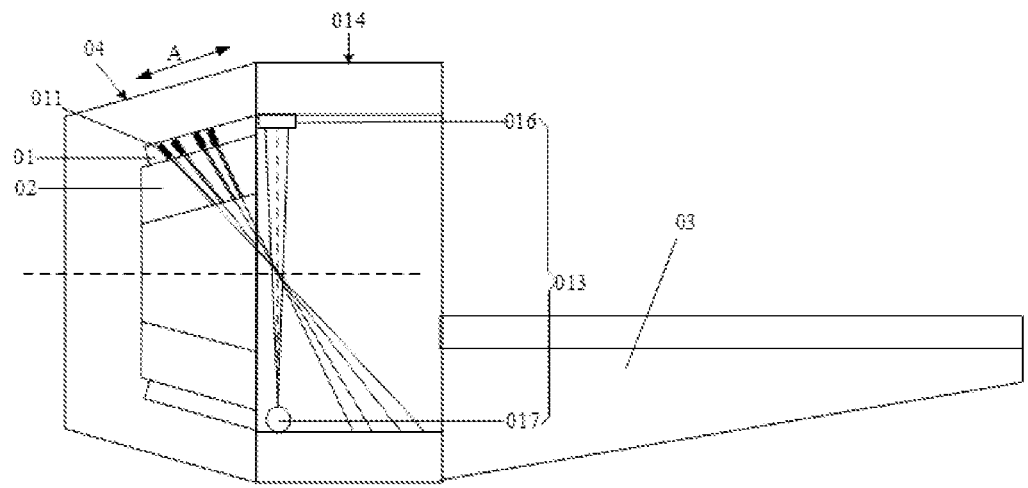
FIG. 11 is a schematic diagram of yet another radiotherapy device provided in an embodiment of the present disclosure.

For example, the radiation source is a radiation source cobalt-60, i.e., the radiation source is the γ-radioactive source, the radiation source apparatus includes a source carrier, the source carrier is provided with a plurality of γ-radioactive sources, and the plurality of γ-radioactive sources are distributed within the preset included angle range in the longitude direction. For example, in the radiotherapy device shown in FIG. 6 and FIG. 7, a source carrier 01 in a radiation source apparatus 4 may be shown in FIG. 4, the source carrier 01 is provided with a plurality of γ-radioactive sources 011, and radiation beams emitted from the plurality of γ-radioactive sources 011 intersect at a common focus 012 in FIG. 6 and FIG. 7. A collimator 02 may be shown in FIG. 5. Both the source carrier 01 in FIG. 4 and the collimator 02 in FIG. 5 are bowl-shaped, the longitude direction of the source carrier is shown by an arrow in FIG. 4, and the longitude direction is a direction of longitude 0 degree to 360 degrees. Alternatively, in the radiotherapy device shown in FIG. 10, a radiation source apparatus 04 may also be barrel-shaped, the source carrier 01 in the radiotherapy device may be shown in FIG. 8, the collimator 02 may be shown in FIG. 9, and both the source carrier and the collimator are barrel-shaped. The longitude direction of the source carrier is shown by an arrow in FIG. 8, and is the direction of longitude 0 degree to 360 degrees. FIG. 10 takes both ends of the source carrier of a same size (e.g., outer diameters of the both ends of a same size), and both ends of the collimator of a same size (e.g., outer diameters of the both ends of a same size) as an example. Of course, the sizes may also be different, an example of which is shown in FIG. 11. A specific shape of the radiation source apparatus is not limited in the present disclosure, and the above description is only taken as an example.

Figure 4:
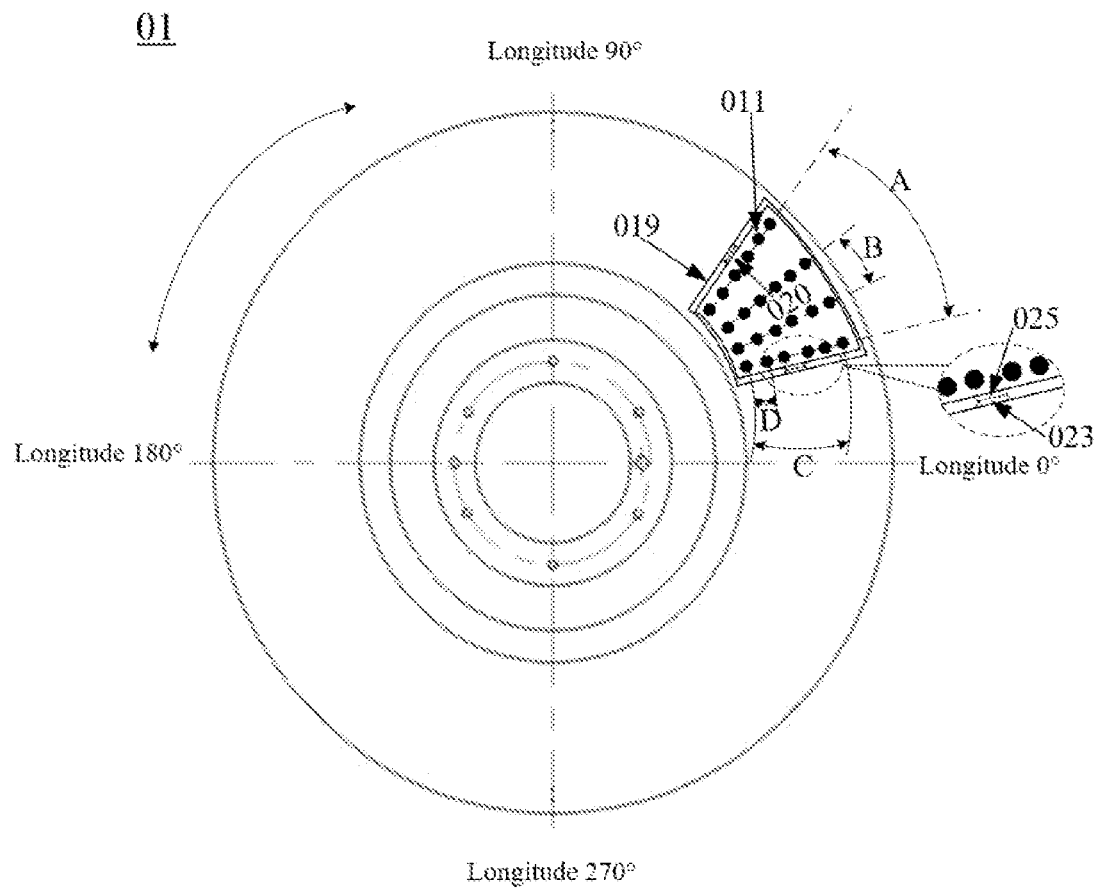
FIG. 4 is a schematic diagram of a source carrier provided in an embodiment of the present disclosure.
Figure 6:
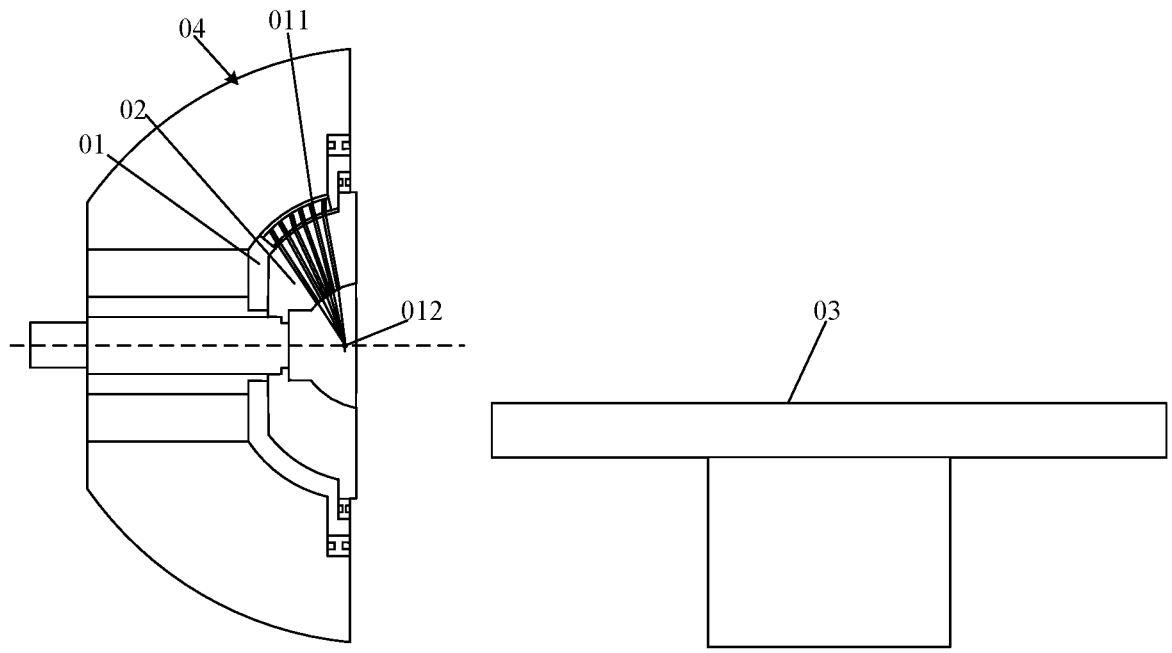
FIG. 6 is a schematic diagram of a radiotherapy device provided in an embodiment of the present disclosure.
Figure 7:
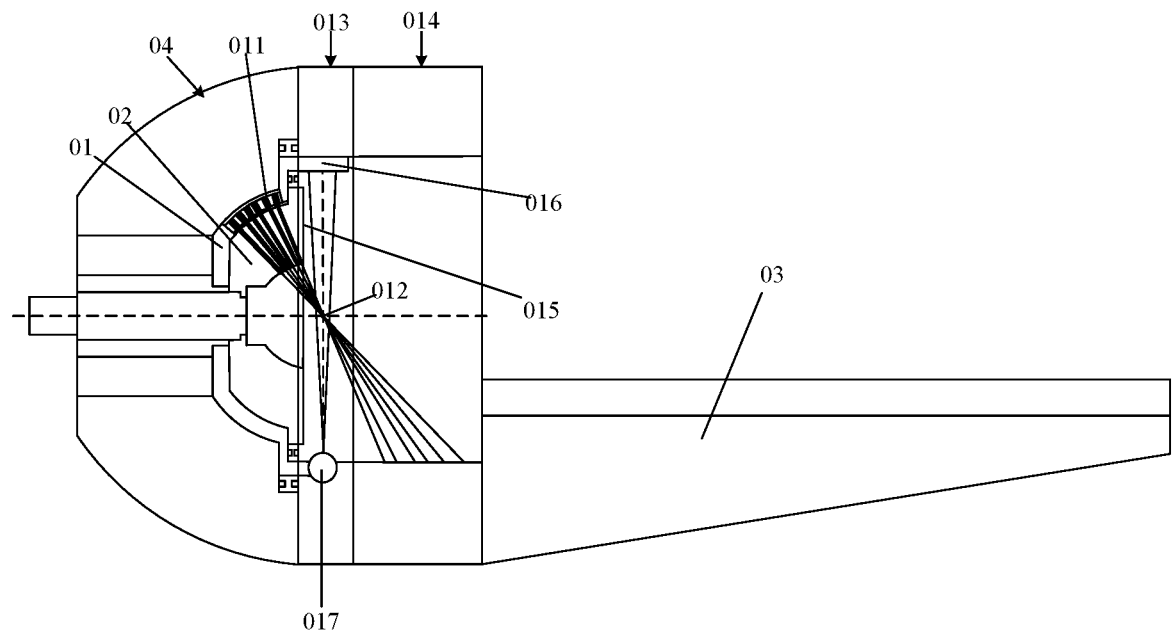
FIG. 7 is a schematic diagram of another radiotherapy device provided in an embodiment of the present disclosure.

The included angle range in the present disclosure is described with the radiotherapy device shown in FIG. 6 and FIG. 7 as an example. As shown in FIG. 4, an included angle of the radiation source 011 in the longitude direction is: an included angle formed with a center of the radiation source 011 as a reference. It should be particularly noted here that if the radiation source 011 includes a row, and centers of a plurality of radiation sources 011 located in a same row are on a same longitude line, then an included angle between the plurality of radiation sources 011 in the longitude direction is considered to be zero degree. In the present disclosure, the preset included angle range is greater than or equal to zero degree. As shown in FIG. 5, an included angle of a collimating hole 021 in the longitude direction is an included angle formed with a center of the collimating hole 021 as a reference. It should be particularly noted here that if the collimating hole 021 includes a row, and centers of a plurality of collimating holes 021 located in a same row are on a same longitude line, then an included angle of the plurality of collimating holes 021 in the longitude direction is considered to be zero degree. In the present disclosure, the preset included angle range is greater than or equal to zero degree.

As shown in FIG. 4, FIG. 4 shows a source carrier 01 provided in the present disclosure. The source carrier 01 is provided with a plurality of radiation sources 011, and an included angle of the plurality of radiation sources 011 in a longitude direction is A. For example, a value range of the included angle A may be 15 degrees to 60 degrees, i.e., 15 degrees≤A≤60 degrees, and the included angle A may be any included angle within the range of 15 degrees to 60 degrees. For example, the range of the included angle A may be 5 degrees to 60 degrees, i.e., 5 degrees≤A≤60 degrees, i.e., the included angle A may be any included angle within the range of 5 degrees to 60 degrees. For example, the included angle A may be 5 degrees, 8 degrees, 10 degrees, 12 degrees, 18 degrees, 20 degrees, 25 degrees, 30 degrees, 40 degrees, 45 degrees, 50 degrees, or 60 degrees. The number and arrangement of the radiation sources 011 are not limited in the present disclosure, and the number of radiation sources may generally be 20 to 180, e.g., may be 30 or 180. Only an example description is provided with 24 radiation sources shown in FIG. 4 as an example.

For example, FIG. 5 shows a bowl-shaped collimator 02 provided in the present disclosure. FIG. 5 takes the collimator 02 provided with 4 collimating hole groups as an example, namely a collimating hole group No. ①, a collimating hole group No. ②, a collimating hole group No. ③, and a collimating hole group No. ④. Each of the collimating hole groups includes 24 collimating holes 021, and corresponds to the distribution of the radiation sources. With the collimating hole group No. ① as an example, radiation beams emitted from the plurality of radiation sources intersect at a common focus after passing through the collimating holes 021 of the collimating hole group No. ①. An included angle of the collimating hole group No. ①, an included angle of the collimating hole group No. ②, an included angle of the collimating hole group No. ③, and an included angle of the collimating hole group No. ④ in the longitude direction are within the preset included angle range. FIG. 5 takes the collimating hole group No. ① as an example. The included angle of the collimating hole group No. ① in the longitude direction (an arrow direction shown in FIG. 5) is A. For example, the included angle A is the same as the included angle of the radiation source 011 of the source carrier 01, which is 5 degrees to 60 degrees.

The collimator 02 is provided with a plurality of collimating hole groups, and the collimator 02 may be provided with two or more than two collimating hole groups. FIG. 5 only provides an example description with the collimator 02 provided with 4 collimating hole groups as an example. Each of the collimating hole groups includes a plurality of collimating holes 021, and the number and arrangement of the plurality of collimating holes 021 correspond to the plurality of radiation sources 011 on the source carrier, such that radiation beams emitted from the radiation sources 011 intersect at a common focus after passing through the collimating holes 021.

Figure 8:
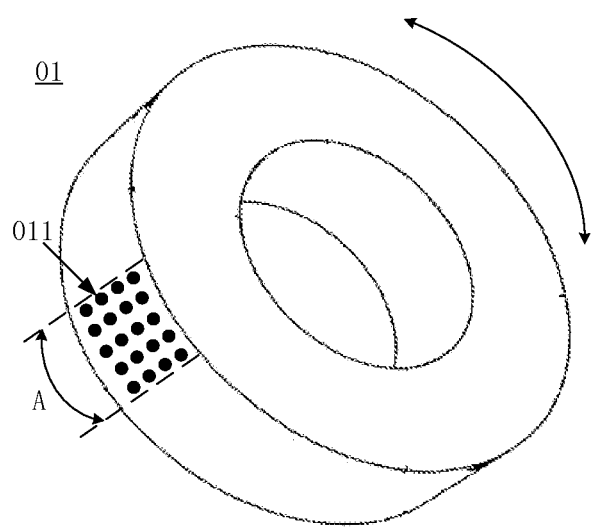
FIG. 8 is a schematic diagram of another source carrier provided in an embodiment of the present disclosure.

For example, as shown in FIG. 10, the radiation source apparatus may also be barrel-shaped. Then, as shown in FIG. 8, the source carrier 01 may also be barrel-shaped as shown in FIG. 8, and its longitude direction is a direction indicated by an arrow in FIG. 8. FIG. 8 takes the barrel-shaped source carrier 01 with both ends of a same size as an example. The specific number and arrangement of the radiation sources 011 are not limited in the present disclosure. FIG. 8 only provides an example description with 20 radiation sources 011 as an example. The collimator 02 may also be barrel-shaped as shown in FIG. 9, and the plurality of collimating holes 021 correspond to the number and arrangement of the radiation sources 011. The description will not be repeated here. The number of collimating hole groups on the collimator 02 is not limited in the present disclosure. FIG. 9 provides an example description by taking the collimator 02 provided with two collimating hole groups and each of the collimating hole groups including 20 collimating holes 021 as an example.

A radiotherapy device provided in the present disclosure includes a radiation source apparatus, the radiation source apparatus includes a plurality of radiation sources and a collimator, source points of the plurality of radiation sources are within a preset included angle range in a longitude direction, the collimator is provided with a plurality of collimating hole groups, and an included angle of each of the collimating hole groups in the longitude direction is within the preset included angle range; and each of the collimating hole groups includes a plurality of collimating holes, and radiation beams emitted from the plurality of radiation sources intersect at a common focus after passing through the collimating holes of the collimating hole groups. Then, the radiotherapy device can drive the plurality of radiation sources through a source carrier to rotate along a center axis of the radiotherapy device. When passing through sensitive tissues or organs, the radiation sources are switched off; while when passing through normal tissues and organs, the radiation sources are switched on, thereby protecting the sensitive tissues and organs, e.g., eyes, from additional damages during the treatment of a head tumor.

The radiotherapy device provided in the present disclosure further includes a driving apparatus configured to drive the radiation source apparatus to move. For example, the driving apparatus may drive the radiation sources to move, and/or drive the collimator to move.

As shown in FIG. 4, a specific example description of the source carrier 01 provided in the present disclosure will be provided below.

For example, in the source carrier 01 provided in the present disclosure, in the longitude direction, the plurality of radiation sources 011 is divided into a plurality of groups, and an included angle range of two adjacent groups of radiation sources 011 is 2 degrees to 15 degrees. For example, among the plurality of radiation sources 011, an included angle of any two adjacent groups of radiation sources 011 is identical, or an included angle of two different adjacent groups of radiation sources 011 is different. This is not limited in the present disclosure. FIG. 4 only shows an example description. As shown in FIG. 4, the plurality of radiation sources 011 is divided into 4 groups. With an included angle B of two adjacent groups of radiation sources 011 (FIG. 4 takes two schematic groups as an example) as an example, the included angle B may range from 2 degrees to 15 degrees, i.e., 2 degrees≤B≤15 degrees, and the included angle B may be any included angle within the range of 2 degrees to 15 degrees. For example, the included angle B may be 2 degrees, 2.5 degrees, 3 degrees, 5 degrees, 6 degrees, 8 degrees, 10 degrees, 12 degrees, or 15 degrees.

In the source carrier 01 provided in the present disclosure, an included angle range of the plurality of radiation sources 011 in a latitude direction is 20 degrees to 60 degrees. For example, as shown in FIG. 4, a plurality of radiation sources 011 is provided within an included angle C of the source carrier 01 in the latitude direction. For example, the included angle C may range from 20 degrees to 60 degrees, i.e., 20 degrees≤C≤60 degrees, and the included angle C may be any included angle within the range of 20 degrees to 60 degrees. For example, the included angle C may be 20 degrees, 25 degrees, 30 degrees, 38 degrees, 40 degrees, 45 degrees, 50 degrees, 53 degrees, or 60 degrees.

For example, for the source carrier 01 provided in the present disclosure, an included angle range of any two adjacent radiation sources 011 is 1 degree to 10 degrees in the latitude direction. For example, among the plurality of radiation sources 011, an included angle of any two adjacent groups of radiation sources 011 is identical in the latitude direction, or an included angle of any two adjacent groups of radiation sources 011 is different in the latitude direction. This is not limited in the present disclosure. FIG. 4 only shows an example description. For example, as shown in FIG. 4, with two of the radiation sources 011 as an example, an included angle of the two radiation sources 011 is D in the latitude direction, the included angle D may range from 1 degree to 10 degrees, i.e., 1 degree≤D≤10 degrees, and the included angle D may be any included angle within the range of 1 degree to 10 degrees. For example, the included angle D may be 1 degree, 2 degrees, 3 degrees, 5 degrees, 6 degrees, 8 degrees, 9 degrees, or 10 degrees.

An example of the source carrier 01 shown in FIG. 4 is that the radiation sources 011 include a plurality of rows in the longitude direction and a plurality of rows in the latitude direction, the radiation sources 011 in a same longitudinal row have the same longitude, and the radiation sources 011 in a same latitudinal row have the same latitude. Further, in order to achieve non-coplanar irradiation and better protect normal tissues, in the source carrier 01 provided in the present disclosure, the radiation sources 011 have different positions in the latitude direction. That is, each of the radiation sources 011 has a different latitude.

The source carrier provided in the present disclosure is provided with a plurality of radiation source holes, and the radiation sources are mounted within the radiation source holes. Alternatively, the source carrier is provided with a source box 020 (reference may be made to FIG. 4) and a source box region 019 conforming to the shape of the source box 020, the source box 020 may be mounted/accommodated in the source box region 019, and the plurality of radiation sources 011 are mounted in the source box 020. The plurality of radiation sources 011 can be pre-mounted in the source box 020, or a package of the source box 020 containing the plurality of radiation sources 011 can be obtained from a supplier. During the assembly of the radiotherapy device, it is only needed to mount the source box 020 containing the radiation sources 011 at the source box region 019. The source box region 019, for example, may be a through hole or blind hole provided in the source carrier, and a plurality of collimating holes are provided on the source carrier, such that radiation beams emitted from the radiation sources may be emitted through the collimating holes. Shapes and structures of the source box and the source box region are not limited in the present disclosure.

The source carrier is further provided with a source box connecting part (i.e., a second connecting part 023 as shown in FIG. 4) configured to fix the source box 020 at the source box region. Similarly, the source box is also provided with a first connecting part 025 as shown in FIG. 4 configured to connect to the source box region. For example, the source carrier and the source box may be connected by screws or clips. The connection and fixing mechanisms of the source box and the source box region are not limited in the present disclosure. Only an exemplary description is provided with the above description as an example.

In the source carrier provided in the present disclosure, the source box is further provided with a connecting part configured to replace the source box. For example, the source box connecting part may be a screw hole, which may be screwed to a source guide part, such as a rod. Alternatively, the source box connecting part and the source guide part may be connected by magnetic force. The connection between the source box and the source guide part and the mechanism of replacing the source box are not limited in the present disclosure. Only an exemplary description is provided with the above description as an example.

The source box and the source carrier provided in the present disclosure are made of different materials. For example, the source box may be formed of a tungsten alloy, and the source carrier may be formed of cast iron.

As shown in FIG. 5, a specific example description of the collimator provided in the present disclosure will be provided below.

In the collimator 02 provided in the present disclosure, a space between two adjacent collimating holes 021 is greater than a size of the radiation source 011 in the longitude direction. Therefore, the collimator 02 may be misaligned with the radiation source 011 only by a small angle, such that the radiation source 011 is shielded by the space between the collimating holes 021, to avoid the use of shielding sites 010 for shielding. Only a small angle is required for misalignment, thus realizing fast switching on/off the source.

For example, for the collimator 02 provided in the present disclosure, each collimating hole group includes a plurality of rows in the longitude direction, and an included angle range of two adjacent rows of radiation sources 011 is 2 degrees to 15 degrees. For example, among the collimating hole groups, an included angle of any two adjacent rows is identical, or an included angle of two different adjacent rows is different. This is not limited in the present disclosure. FIG. 5 only shows an example description. As shown in FIG. 5, the plurality of radiation sources 011 is divided into 4 rows. With an included angle B of adjacent rows of collimating holes (FIG. 9 takes two schematic rows as an example) as an example, the included angle B may range from 2 degrees to 15 degrees, i.e., 2 degrees≤B≤15 degrees, and the included angle B may be any included angle within the range of 2 degrees to 15 degrees. For example, the included angle B may be 2 degrees, 2.5 degrees, 3 degrees, 5 degrees, 6 degrees, 8 degrees, 10 degrees, 12 degrees, or 15 degrees.

In the collimator 02 provided in the present disclosure, an included angle range of the collimating hole group in the latitude direction is 20 degrees to 60 degrees. For example, as show in FIG. 5, the included angle C may range from 20 degrees to 60 degrees, i.e., 20 degrees≤C≤60 degrees, and the included angle C may be any included angle within the range of 20 degrees to 60 degrees. For example, the included angle C may be 20 degrees, 25 degrees, 30 degrees, 38 degrees, 40 degrees, 45 degrees, 50 degrees, 53 degrees, or 60 degrees.

For example, in the collimator 02 provided in the present disclosure, an included angle range of any two adjacent collimating holes 021 is 1 degree to 10 degrees in the latitude direction. For example, an included angle of any two adjacent collimating holes 021 is identical in the latitude direction, or an included angle of any two adjacent collimating holes 021 is different in the latitude direction. This is not limited in the present disclosure. FIG. 5 only shows an example description. For example, as shown in FIG. 5, with two of the collimating holes as an example, an included angle of the two collimating holes is D in the latitude direction, the included angle D may range from 1 degree to 10 degrees, i.e., 1 degree≤D≤10 degrees, and the included angle D may be any included angle within the range of 1 degree to 10 degrees. For example, the included angle D may be 1 degree, 2 degrees, 3 degrees, 5 degrees, 6 degrees, 8 degrees, 9 degrees, or 10 degrees.

An example of the collimator 02 shown in FIG. 5 is that the collimating holes 021 of the collimating hole group include a plurality of rows in the longitude direction and a plurality of rows in the latitude direction, the radiation sources 011 in a same longitudinal row have the same longitude, and the radiation sources 011 in a same latitudinal row have the same latitude. Further, in order to achieve non-coplanar irradiation and better protect normal tissues, in the source carrier 01 provided in the present disclosure, the collimating holes 021 have different positions in the latitude direction. That is, any two collimating holes 021 have different latitudes.

In the collimator 02 provided in the present disclosure, the collimator 02 further includes shielding sites 010 configured to shield the radiation beams from the plurality of radiation sources 011. That is, rays from the radiation sources 011 may be shielded by the shielding sites 010 of the collimator 02, to realize switching off the source. Specific positions of the shielding sites 010 are not limited in the present disclosure. FIG. 5 provides an example description with the positions of the shielding sites 010 opposite to the positions of the collimating hole groups as an example.

For example, in the collimator 02 provided in the present disclosure, the shielding sites 010 are located between any two adjacent collimating hole groups among the plurality of collimating hole groups. For example, as shown in FIG. 12, an example description is provided with the shielding sites 010 located between the collimating hole group No. ② and the collimating hole group No. ③ as an example.

Figure 12:
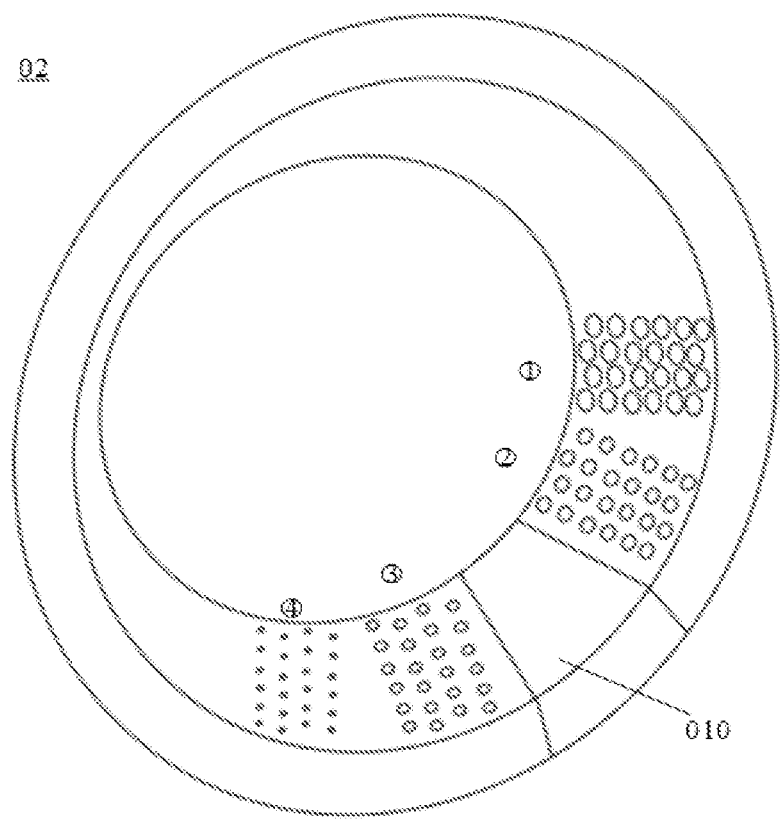
FIG. 12 is a schematic diagram of another collimator provided in an embodiment of the present disclosure.

FIG. 12 only takes one shielding site 010 being included as an example. The collimator 02 provided in the present disclosure includes a plurality of shielding sites 010. For example, the shielding sites 010 may also be provided between the collimating hole group No. ① and the collimating hole group No. ②. The shielding sites 010 may also be provided between the collimating hole group No. ③ and the collimating hole group No. ④. The shielding sites 010 may also be provided between two adjacent collimating hole groups. The number and distribution of the plurality of shielding sites 010 are not limited in the present disclosure. Only an example description is provided with the above description as an example.

The collimator 02 provided in the present disclosure is provided with a shielding body 05 at the shielding site 010, and a material density of the shielding body 05 is greater than a material density of the collimator 02. For example, the shielding body 05 is connected to the collimator 02, and the shielding body 05 may be made of a tungsten block or a lead alloy or an alloy thereof. The collimator 02 may be made of cast iron. Therefore, the shielding body 05 can achieve better shielding of the radiation sources 011. The positions of the shielding sites 010 are not limited in the present disclosure. An example is shown in FIG. 12, or the shielding sites may also be located between different collimating hole groups.

In the collimator 02 provided in the present disclosure, the collimator 01 includes an inner collimator and an outer collimator that are connected, and collimating holes of the inner collimator and collimating holes of the outer collimator are arranged correspondingly. That is, the collimator may include double layers, and the inner collimator and the outer collimator may be connected and fixed by screws.

The collimator provided in the present disclosure includes an inner collimator and an outer collimator, and the inner collimator and the outer collimator are relatively rotatable. For example, if an accident occurs during treatment, the source may be fast switched off through the inner collimator, then the shielding sites may be aligned with the radiation sources by rotating the outer collimator to shield the radiation sources, and then shielding sites of the inner collimator may be further aligned with the radiation sources to achieve completely switching off the source.

In the collimator provided in the present disclosure, the collimating holes of the inner collimator are taper holes, and/or the collimating holes of the outer collimator are straight holes. For example, the collimating holes of the inner collimator may be straight holes, and the collimating holes of the outer collimator may also be straight holes; or the collimating holes of the inner collimator may be taper holes, while the collimating holes of the outer collimator may be straight holes; or the collimating holes of the inner collimator and the collimating holes of the outer collimator may all be taper holes.

Figure 13:
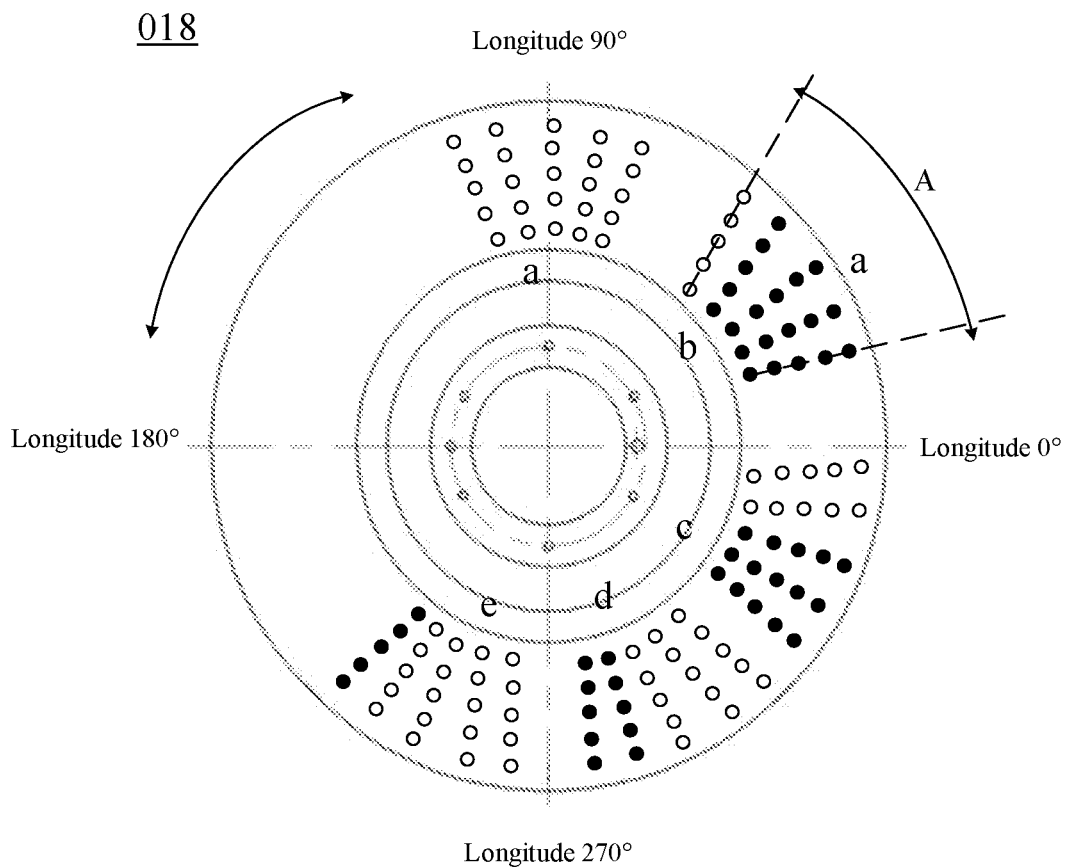
FIG. 13 is a schematic diagram of a switch body provided in an embodiment of the present disclosure.

In a radiotherapy device provided in the present disclosure, the radiation source apparatus further includes a switch body, the switch body is located between the source carrier and the collimator; and the switch body is provided with at least two sets of hole sites corresponding to the radiation sources, where one set of hole sites include a through hole, and each of the rest sets of the hole sites includes a through hole and a shielding site. For example, as shown in FIG. 13, a switch body 018 is provided with 5 sets of hole sites, namely a to e sets of hole sites, where hole sites a are all through holes, only one row of hole sites b are through holes while all other hole sites b are shielding sites, two rows of hole sites c are through holes while all other hole sites c are shielding sites, three rows of hole sites d are through holes while all other hole sites d are shielding sites, and four rows of hole sites e are through holes while all other hole sites e are shielding sites. It should be noted that the shielding sites may be the switch body provided with no holes, or the switch body provided with holes but the holes may be filled with tungsten rods to shield the radiation sources.

In the radiotherapy device provided in the present disclosure, a space between two adjacent collimating holes is greater than a size of the radiation source in the longitude direction. Therefore, the collimator may be misaligned with the radiation sources only by a small angle, such that the radiation sources are shielded by the space between the collimating holes, to avoid the use of the shielding sites for shielding. Only a small angle is required for misalignment, thus realizing fast switching on/off the source.

Figure 3:
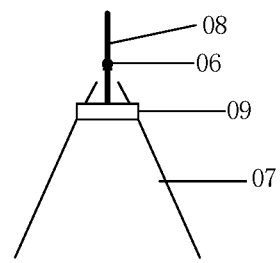
FIG. 3 is a schematic principle diagram of an X-ray beam provided in an embodiment of the present disclosure.

In the radiotherapy device provided in the present disclosure, the radiation beams are the X-ray beams, and the radiotherapy device includes one or a plurality of X-ray accelerating systems; the one X-ray accelerating system emits a plurality of X-ray beams in a beam emission angle range; or the plurality of X-ray accelerating systems emits a plurality of X-ray beams in the beam emission angle range. The X-ray accelerating systems generate the X-ray beams by hitting a target body with an electron beam. A source point 06 of the radiation source in the present disclosure may be an intersection point of reverse extension lines of X-ray beams 07 as shown in FIG. 3. The X-ray beams 07 may be obtained by irradiating a target body 09 with an electron beam 08. Then, the radiotherapy device in the present disclosure may include one X-ray accelerating system that emits an electron beam, and the electron beam hits different target bodies or different positions of a target body to emit a plurality of X-rays. Alternatively, the radiotherapy device may include a plurality of X-ray accelerating systems, each of the X-ray accelerating systems emits an electron beam respectively, and the electron beam hits a target body to emit a plurality of X-rays. The description on a specific structure of the X-ray beams emitted from an accelerator will not be repeated in the present disclosure.

During treatment, a tumor of a patient is required to be precisely located at a common focus such that radioactive rays will kill tumor cells. However, if the patient moves during treatment, then the radioactive rays will deviate, which not only goes against the treatment but also is harmful to the health of the patient. Because the common focus of the radiotherapy device in related technologies is located within a cavity of the radiation source apparatus, it is impossible to monitor whether the head of the patient moves during treatment. In the radiotherapy device provided in the present disclosure, the common focus is located outside an end surface of the radiation source apparatus. For example, as shown in FIG. 7, FIG. 10, and FIG. 11, the common focus 012 is located outside the end surface of the radiation source apparatus 04, which contributes to observing and monitoring whether the patient moves during treatment.

The radiotherapy device provided in the present disclosure further includes an imaging apparatus, the imaging apparatus is arranged on a side of the radiation source apparatus along a center axis direction of the radiation source apparatus, and the common focus is located within an imaging region of the imaging apparatus. That is, the tumor of the patient located within the imaging region may be imaged through the imaging apparatus, to determine whether the patient is displaced based on the image. The displacement is monitored precisely based on the image.

In the radiotherapy device of the present disclosure, the imaging apparatus includes any one of an X-ray imaging apparatus, a CT imaging apparatus, an ultrasonic imaging apparatus, a DSA imaging apparatus, a MR imaging apparatus, or a PET imaging apparatus, or any combination thereof. For example, the imaging apparatus is the X-ray imaging apparatus. For example, as shown in FIG. 7, FIG. 10, and FIG. 11, the imaging apparatus 013 may include an X-ray bulb tube 017 and a flat panel detector 016, or may include two X-ray bulb tubes and two flat panel detectors, and radiation beams emitted from the two X-ray bulb tubes intersect. Of course, the imaging apparatus may also be a combination of any two or more different imaging apparatuses. For example, the imaging apparatus may be a combination of the X-ray imaging apparatus and the DSA imaging apparatus. A specific setting of the imaging apparatus is not limited in the present disclosure, and only an example description is provided with the above description as an example.

For example, in the case where the imaging apparatus includes an imaging center point, the common focus 012 overlaps with the imaging center point. For example, the imaging apparatus includes two X-ray bulb tubes and two corresponding X-ray flat panels receiving radiation beams emitted from each of the X-ray bulb tubes, and the radiation beams emitted from the two X-ray bulb tubes intersect at the common focus.

In the radiotherapy device provided in the present disclosure, the imaging apparatus is rotatable along a center axis of the radiation source apparatus. As shown in FIG. 7, FIG. 10, and FIG. 11, if the imaging apparatus 013 includes an X-ray bulb tube 017 and an X-ray flat panel 016, then whether the patient moves in upward and downward directions as shown in FIG. 7, FIG. 10, and FIG. 11 cannot be determined based on the image. Therefore, if the imaging apparatus rotates along the center axis of the radiation source apparatus, then the imaging apparatus can acquire images of the patient at different angles, thereby determining whether the patient moves at each angle.

The imaging apparatus may rotate by installing a rotating apparatus in the imaging apparatus, e.g., a gear ring, or by slip ring driving. A driving approach of the imaging apparatus is not limited in the present disclosure.

In the radiotherapy device provided in the present disclosure, the imaging apparatus is connected to the radiation source apparatus. For example, the imaging apparatus is connected to either of the source carrier or the collimator. With FIG. 7 as an example, the ray bulb tube 017 and the X-ray flat panel 016 may be connected to the source carrier, such that the rotation of the source carrier drives the imaging apparatus to rotate, thereby avoiding separately providing a rotation driving apparatus for the imaging apparatus. Of course, the imaging apparatus may also be connected to the switch body or the collimator. This is not limited in the present disclosure.

In a radiotherapy device provided in the present disclosure, the radiotherapy device further includes a shielding apparatus, the shielding apparatus is located on a side of the radiation source apparatus, and the radiation beams emitted from the radiation sources are shielded by the shielding apparatus after passing through the common focus. For example, as shown in FIG. 7, FIG. 10, and FIG. 11, the shielding apparatus 014 is located on a side of the common focus 012 of the radiation source apparatus 04, and the radiation beams emitted from the radiation sources 011 are shielded by the shielding apparatus 014 after passing through the common focus 012, thereby avoiding unnecessary radiation in the treatment chamber. For example, if the shielding apparatus is ring-shaped, then the rays emitted from the radiation sources, when rotating around the center axis for one cycle, are all received by the shielding apparatus. Alternatively, the shielding apparatus is a shielding block, which is rotatable along the center axis of the radiation source apparatus, to follow the rotation of the radiation sources to receive the rays passing through the common focus. It should be noted that if the treatment couch carries the patient to move, then a channel is provided on the shielding apparatus to facilitate the movement of the treatment couch.

For example, position settings of the shielding apparatus and the imaging apparatus are not limited in the present disclosure. For example, the imaging apparatus may be separately arranged, or may be arranged inside the shielding apparatus.

The radiotherapy device provided in the present disclosure further includes a shielding door which can switch on or off a cavity of the radiotherapy device. With FIG. 7 as an example, the shielding door 015 may be arranged outside the cavity of the radiation source apparatus 04, and can open or close the cavity of the radiation source apparatus 04, which may be opened/closed upward and downward, or leftward and rightward. Therefore, during non-treatment time, the radiation beams can be shielded by the shielding door. Of course, the shielding door may also be arranged between the imaging apparatus and the shielding apparatus, or the shielding door may be arranged outside the shielding door. A specific setting position of the shielding door 015 is not limited in the present disclosure, and only an example description is provided with FIG. 7 as an example.

In the radiotherapy device provided in the present disclosure, as shown in FIG. 6, an anti-sinking component (not shown in the figure) is also provided between the collimator 02 and the source carrier 01. Further, the radiation source apparatus further includes the shielding body 05 located outside the source carrier 01, and an anti-sinking component is also provided between the shielding body 05 and the source carrier 01. For example, the anti-sinking component may be a bearing, thereby avoiding sagging at the other end when the collimator and the source carrier are driven to rotate at one end.

For a control driving method for a radiotherapy device provided in the present disclosure, the radiotherapy device includes a plurality of radiation sources, source points of the plurality of radiation sources are within a preset included angle range in a longitude direction.

Figure 14:
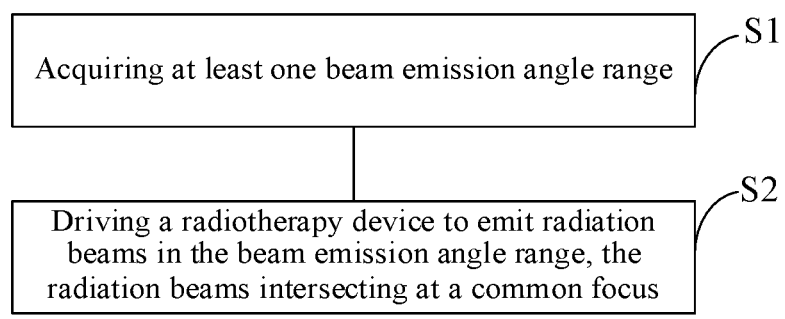
FIG. 14 is a schematic diagram of a control driving method provided in an embodiment of the present disclosure.

It should be noted that in the present disclosure, the radiation source may be an X-ray accelerating system, and then the radiation beam is an X-ray beam; or the radiation source may be a γ-radioactive source, and then the radiation beam is a γ-ray beam. If the radiation beam is the X-ray beam, and its principle is that an electron beam hits a target body to generate the X-ray beam, then a source point of the radiation source may be an intersection point of reverse extension lines of X-ray beams 07 as shown in FIG. 14. If the radiation beam is the γ-ray beam, then the source point of the radiation source may be an isotope radiation source, e.g., cobalt-60.

As shown in FIG. 14, the control driving method includes:

Step S1: acquiring at least one beam emission angle range.

Step S2: driving a radiotherapy device to emit radiation beams in the beam emission angle range, the radiation beams intersecting at a common focus.

Figure 15:
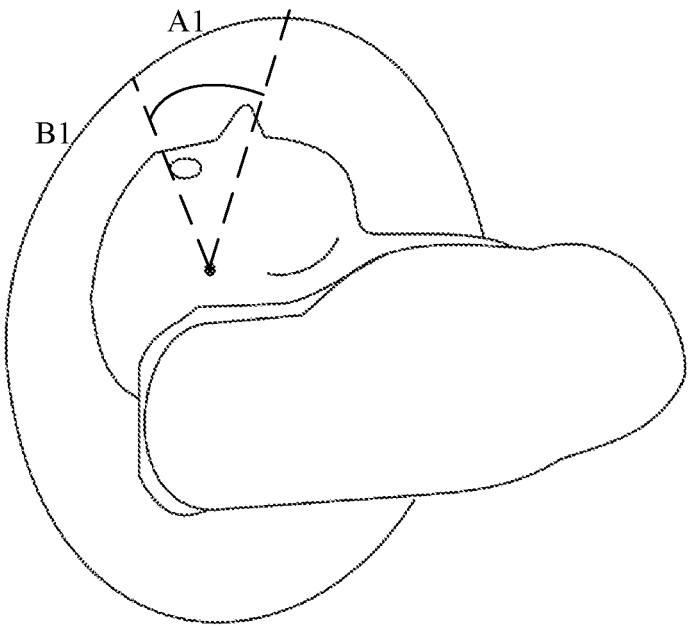
FIG. 15 is a schematic diagram of irradiation treatment provided in an embodiment of the present disclosure.

It should be noted that since a driving apparatus in the radiotherapy device is generally provided with a preset zero position, the zero position is used as a reference during radiotherapy to determine a driving angle range for driving. In the present disclosure, the beam emission angle range may be an angle range that is required for a radiotherapy device to emit radiation beams for irradiation treatment and is included in a corresponding treatment plan formulated by a therapist based on a tumor image of a patient, and the angle range is a driving angle range of the driving apparatus. For example, as shown in FIG. 15, in the corresponding treatment plan formulated by the therapist based on the tumor image of the patient, the radiotherapy device performs irradiation treatment in a region B1 and does not perform irradiation treatment in a region A1 (the region A1 is an irradiated region including two eyes to prevent the rays from damaging the optic nerves). Then, the beam emission angle range is a driving angle range of the driving apparatus driving the radiation sources to irradiate in the region B1, and a protection angle range is a driving angle range of the driving apparatus driving the radiation sources to avoid irradiation in the region A1. During radiotherapy, rotational irradiation is only required within the driving angle range of irradiation in the region B1, thereby avoiding irradiating the eyes and damaging the sensitive tissues. For example, the driving angle range is a rotation angle of a motor. Further, in the present disclosure, if the radiotherapy device rotates for more than 360 degrees, then the driving angle range also exceeds 360 degrees. Alternatively, if the radiotherapy device rotates for more than 360 degrees, then the number of rotation cycles and driving angle ranges corresponding to different numbers of rotation cycles are calibrated.

Of course, during radiotherapy, rotational irradiation may also be performed in both of the corresponding regions A1 and B1, and then the beam emission angle range is the driving angle range for irradiation in the region A1 and the region B1, e.g., 360 degrees. In this case, a dose received by the sensitive tissues, e.g., the optic nerves, may be reduced by reducing the irradiation duration, thereby protecting the sensitive tissues and organs.

For a control driving method provided in the present disclosure, a radiotherapy device includes a plurality of radiation sources, and source points of the plurality of radiation sources are within a preset included angle range in a longitude direction. The control driving method includes: acquiring at least one beam emission angle range, and driving the radiotherapy device to emit radiation beams in the beam emission angle range, the radiation beams intersecting at a common focus, thereby protecting the sensitive tissues and organs, e.g., eyes, from additional damages during the treatment of a head tumor.

Figure 16:
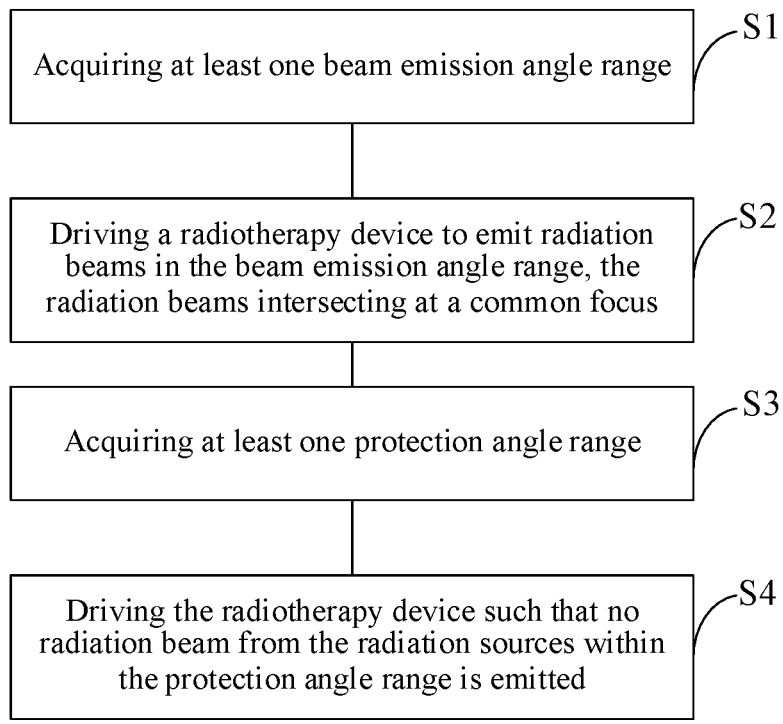
FIG. 16 is a schematic diagram of another control driving method provided in an embodiment of the present disclosure.

As shown in FIG. 16, a control driving method provided in the present disclosure further includes:

Step S3: acquiring at least one protection angle range. The at least one protection angle range is less than 360 degrees.

Figure 17:
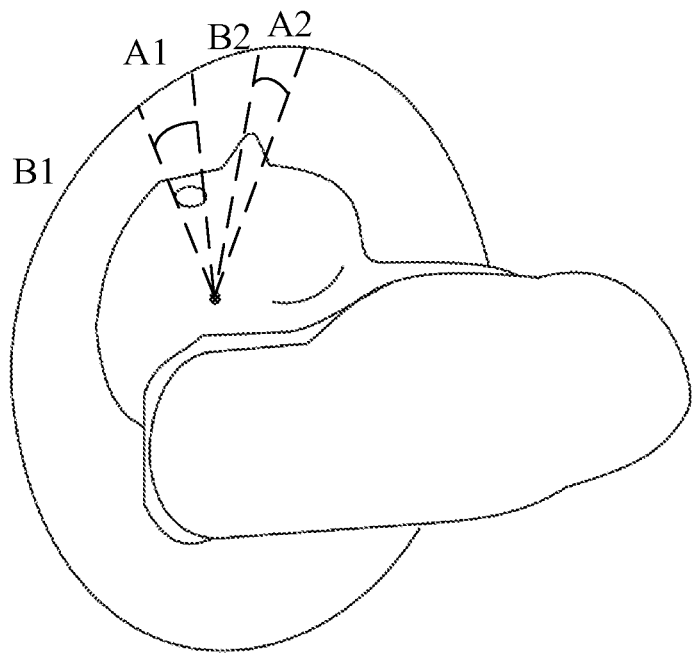
FIG. 17 is a schematic diagram of another irradiation treatment provided in an embodiment of the present disclosure.

As shown in FIG. 17, the radiotherapy device performs irradiation treatment in a region B1 and a region B2, and does not perform irradiation treatment in a region A1 and a region A2 (the region A1 corresponds to a region where one eye is located, and the region A2 corresponds to a region where the other eye is located, to prevent the rays from damaging the optic nerves). Then, the beam emission angle range is a driving angle range of the driving apparatus driving the radiation sources to irradiate in the region B1 and the region B2, and a protection angle range is a driving angle range of the driving apparatus driving the radiation sources to avoid irradiation in the region A1 and the region A2.

Step S4: driving the radiotherapy device such that no radiation beam from the radiation sources within the protection angle range is emitted.

For a control driving method provided in the present disclosure, a radiotherapy device includes a plurality of radiation sources, and source points of the plurality of radiation sources are within a preset included angle range in a longitude direction. The control driving method includes: acquiring at least one beam emission angle range and at least one protection angle range, and driving the radiotherapy device to emit radiation beams in the beam emission angle range, the radiation beams intersecting at a common focus, such that no radiation beam from the radiation sources within the protection angle range is emitted, thereby protecting the sensitive tissues and organs, e.g., eyes, from additional damages during the treatment of a head tumor.

For example, at least one of the beam emission angle range is adjacent to one of the protection angle range. As shown in FIG. 17, irradiation treatment is performed in the regions B1 and B2, and no irradiation treatment is performed in the regions A1 and A2. Since the region B1 is adjacent to the region A1, the beam emission angle range corresponding to the region B1 is adjacent to the protection angle range corresponding to the region A1.

The control driving method provided in the present disclosure includes: acquiring a plurality of beam emission angle ranges, and the radiotherapy device operates at different speeds within at least two of the beam emission angle ranges. For example, referring to FIG. 17, irradiation treatment is performed in the regions B1 and B2, then the beam emission angle range corresponding to the region B1 and the beam emission angle range corresponding to the region B2 are acquired, the radiotherapy device operates at a speed of V1 in the beam emission angle range corresponding to the region B1, and at a speed of V2 in the beam emission angle range corresponding to the region B2, V1≠V2, such that speed can be controlled to adjust the irradiation duration at different positions, and then adjust the dose at the focus.

For example, as show in FIG. 15, during radiotherapy, rotational irradiation is performed in both of the corresponding regions A1 and B1, and then the beam emission angle range is the driving angle range for irradiation in the region A1 and the region B1. The speed may be V1 in the beam emission angle range corresponding to the region B1, and V2 in the beam emission angle range corresponding to the region A1, V1<V2. That is, the speed in the region A1 is greater than the speed in the region B1, thereby reducing the dose received by the sensitive tissues within the region A1, to protect the sensitive tissues and organs.

It should be noted that the driving angle range in the present disclosure is the rotation angle of the motor, and the driving angle range also exceeds 360 degrees. For example, if the motor exceeds 360 degrees, then the number of rotation cycles and driving angle ranges corresponding to different numbers of rotation cycles are calibrated. The radiotherapy device operates at different speeds within at least two of the beam emission angle ranges, and may be driven at different driving speeds in a same corresponding irradiated region at different numbers of rotation cycles. For example, a planned treatment duration of radiotherapy is 2 minutes, and it takes 1 minute for the motor to be driven and rotate for one cycle. As shown in FIG. 17, a driving speed for irradiation in the region B1 is V1 in the beam emission angle range in a first cycle, and a driving speed for irradiation in the region B1 is V2 in the beam emission angle range in a second circle, V1≠V2.

For the control driving method provided in the present disclosure, for example, as shown above, the two beam emission angle ranges corresponding to different speeds are adjacent.

For the control driving method provided in the present disclosure, the radiotherapy device is driven to reciprocate within the beam emission angle range. For example, if only one beam emission angle range is acquired, then the radiotherapy device can reciprocate within the beam emission angle range to increase the dose received by the tumor. Of course, if a plurality of beam emission angle ranges is acquired, the radiotherapy device can also reciprocate within the beam emission angle ranges to increase the dose received by the tumor.

For the control driving method provided in the present disclosure, the radiation beams are γ-ray beams or X-ray beams. The two different radiation beams will be described below respectively.

For the control driving method provided in the present disclosure, the radiation sources are γ-radioactive sources, the radiotherapy device includes a source carrier and a collimator, the source carrier is provided with a plurality of γ-radioactive sources, the plurality of γ-radioactive sources are distributed within the preset included angle range in a longitude direction, the collimator is provided with a plurality of collimating hole groups, and each of the collimating hole groups is distributed within the preset included angle range in the longitude direction. That is, the radiotherapy device may be the radiotherapy device as shown in FIG. 6, FIG. 7, FIG. 10, and FIG. 11. Then, step S2 as shown in FIG. 14 and FIG. 16 specifically includes: driving the radiotherapy device such that radiation beams emitted from the plurality of γ-radioactive sources are emitted after passing through collimating holes of the collimator, and intersect at a common focus. For example, the source carrier and the collimator may be driven to rotate, such that the radiation sources on the source carrier are emitted after passing through collimating holes of the collimator, and intersect at a common focus.

For the control driving method provided in the present disclosure, the radiation sources are γ-radioactive sources, the radiotherapy device includes a source carrier and a collimator, the source carrier is provided with a plurality of γ-radioactive sources, the plurality of γ-radioactive sources are distributed within the preset included angle range in a longitude direction, the collimator is provided with a plurality of collimating hole groups, and each of the collimating hole groups is distributed within the preset included angle range in the longitude direction. Likewise, the radiotherapy device may be the radiotherapy device as shown in FIG. 6, FIG. 7, FIG. 10, and FIG. 11. Then, step S4 as shown in FIG. 16 specifically includes: driving the radiotherapy device such that the radiation beams emitted from the plurality of γ-radioactive sources are shielded by the collimator. For example, the source carrier and the collimator may be driven to be misaligned, such that the radiation sources on the source carrier are shielded by a gap between the collimating holes of the collimator. The source carrier is only required to be misaligned with the collimator by rotating a small angle, thereby realizing fast switching on/off the source; or the source carrier and the collimator may be driven to be misaligned, such that the radiation sources on the source carrier are shielded by the shielding sites of the collimator.

For the control driving method provided in the present disclosure, the radiotherapy device further includes a source switch body, i.e., the source switch body is configured to switch on/off the source. Then, step S4 as shown in FIG. 16 specifically includes: driving the radiotherapy device such that the radiation beams emitted from the plurality of γ-radioactive sources are shielded by the source switch body. Further, the source switch body is provided on the collimator, i.e., the source switch body may be located at positions of the shielding sites of the collimator.

For the control driving method provided in the present disclosure, the radiotherapy device further includes a switch body, the switch body is located between the source carrier and the collimator, and the switch body is provided with at least two sets of hole sites corresponding to the γ-radioactive sources, where one set of hole sites are all through holes, and each of the rest sets of the hole sites includes through hole sites and shielding sites. With FIG. 14 as an example, as shown in FIG. 18, the control driving method further includes:

Step S5: driving a switch body such that a part of the radiation beams emitted from a plurality of γ-radioactive sources are shielded by shielding sites of the switch body.

Figure 18:
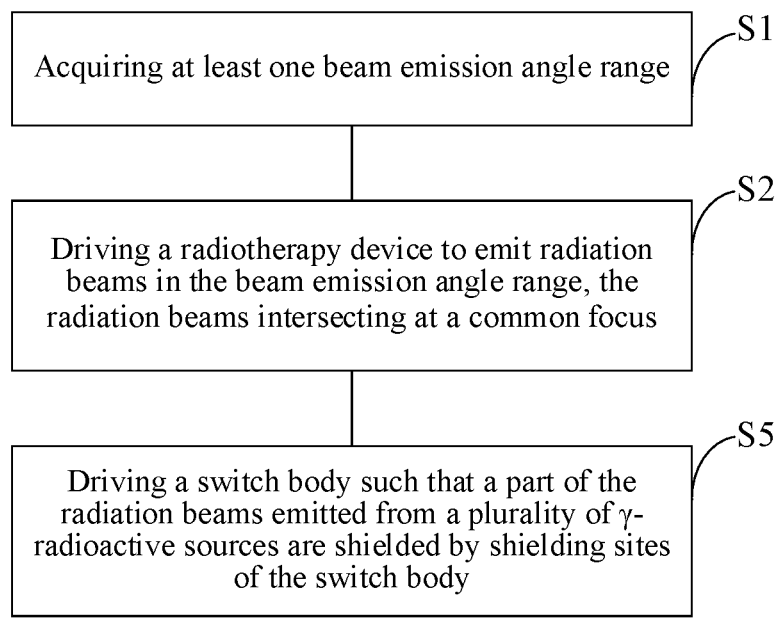
FIG. 18 is a schematic diagram of still another control driving method provided in an embodiment of the present disclosure.

Of course, the control driving method as shown in FIG. 16 may also include step S5, and FIG. 18 only takes the control driving method shown in FIG. 14 including step S5 as an example.

The switch body is shown in FIG. 13. The switch body 018 is driven, such that a part of the radiation beams emitted from the plurality of γ-radioactive sources are shielded by the shielding sites of the switch body, i.e., a part of the radiation beams from the radiation sources can be shielded by the shielding sites of the switch body, thereby achieving the purpose of adjusting the dose.

For the control driving method provided in the present disclosure, a space between two adjacent collimating holes in a same collimating hole group is greater than a size of the γ-radioactive source in the longitude direction. Then, step S4 as shown in FIG. 16 specifically includes: driving the radiotherapy device such that the plurality of γ-radioactive sources is misaligned with the collimating holes, where a part of the radiation beams emitted from the γ-radioactive sources are shielded by edge regions of the collimating hole group, and the rest of the radiation beams emitted from the γ-radioactive sources are shielded by a space region between the collimating holes. For example, the source carrier and the collimator may be driven to be misaligned, such that the radiation sources on the source carrier are shielded by a gap between the collimating holes of the collimator. The source carrier is only required to be misaligned with the collimator by rotating a small angle, thereby realizing fast switching on/off the source.

For the control driving method provided in the present disclosure, the radiation beams are the X-ray beams, and the radiotherapy device includes one or a plurality of X-ray accelerating systems.

When the radiotherapy device includes one X-ray accelerating system, step S2 as shown in FIG. 14 or FIG. 16 specifically includes: driving the one X-ray accelerating system to emit a plurality of X-ray beams in the beam emission angle range.

Further, step S4 as shown in FIG. 16 specifically includes: switching off all or a part of the X-ray beams from one X-ray accelerating system. For example, switching off the X-ray accelerating system may be switching off all or a part of the X-ray beams by switching off a microwave apparatus or switching off an accelerating tube.

Alternatively, when the radiotherapy device includes a plurality of X-ray accelerating systems, step S2 as shown in FIG. 14 or FIG. 16 specifically includes: driving a plurality of X-ray accelerating systems to emit a plurality of X-ray beams in the beam emission angle range.

Further, step S4 shown in FIG. 16 specifically includes: switching off all or a part of the plurality of X-ray accelerating systems. For example, switching off the plurality of X-ray accelerating systems may be switching off all or a part of the X-ray beams by switching off the microwave apparatus of the plurality of X-ray accelerating systems or switching off the accelerating tube.

Figure 19:
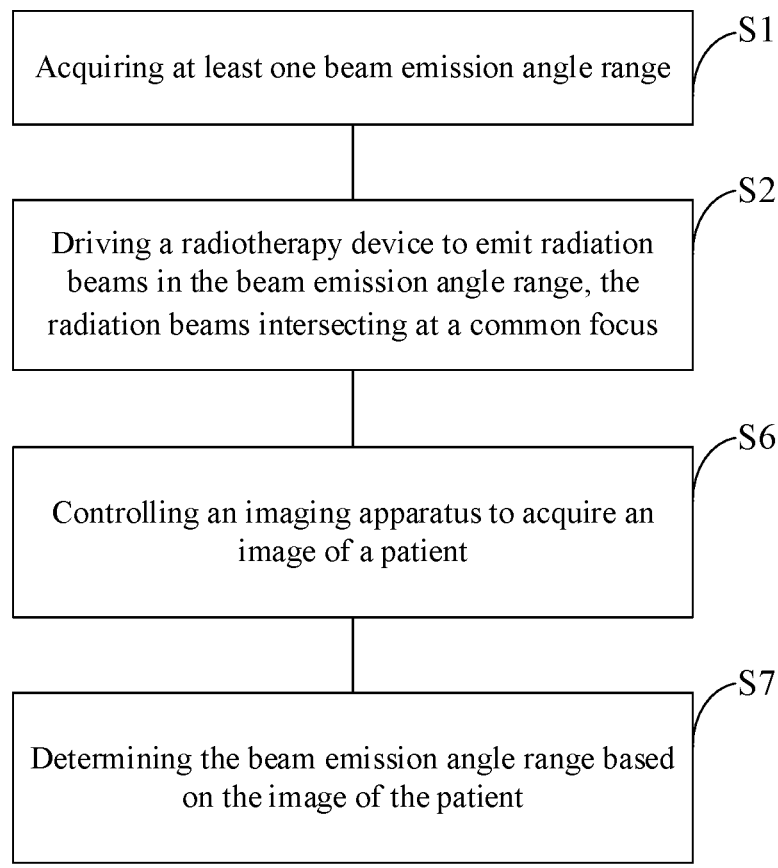
FIG. 19 is a schematic diagram of yet another control driving method provided in an embodiment of the present disclosure.

For example, in the radiotherapy device as shown in FIG. 7, FIG. 10, and FIG. 11, the common focus is located outside an end surface of the radiation source apparatus. The radiotherapy device further includes an imaging apparatus, and the common focus is located within an imaging region of the imaging apparatus. As shown in FIG. 19, the driving control method further includes:

Step S6: controlling an imaging apparatus to acquire an image of a patient.

Step S7: determining the beam emission angle range based on the image of the patient.

It should be noted that the beam emission angle range in step S1 may be a beam emission angle range determined by a therapist based on the image of the patient before radiotherapy, and may be determined or adjusted based on the acquired image during treatment.

Figure 20:
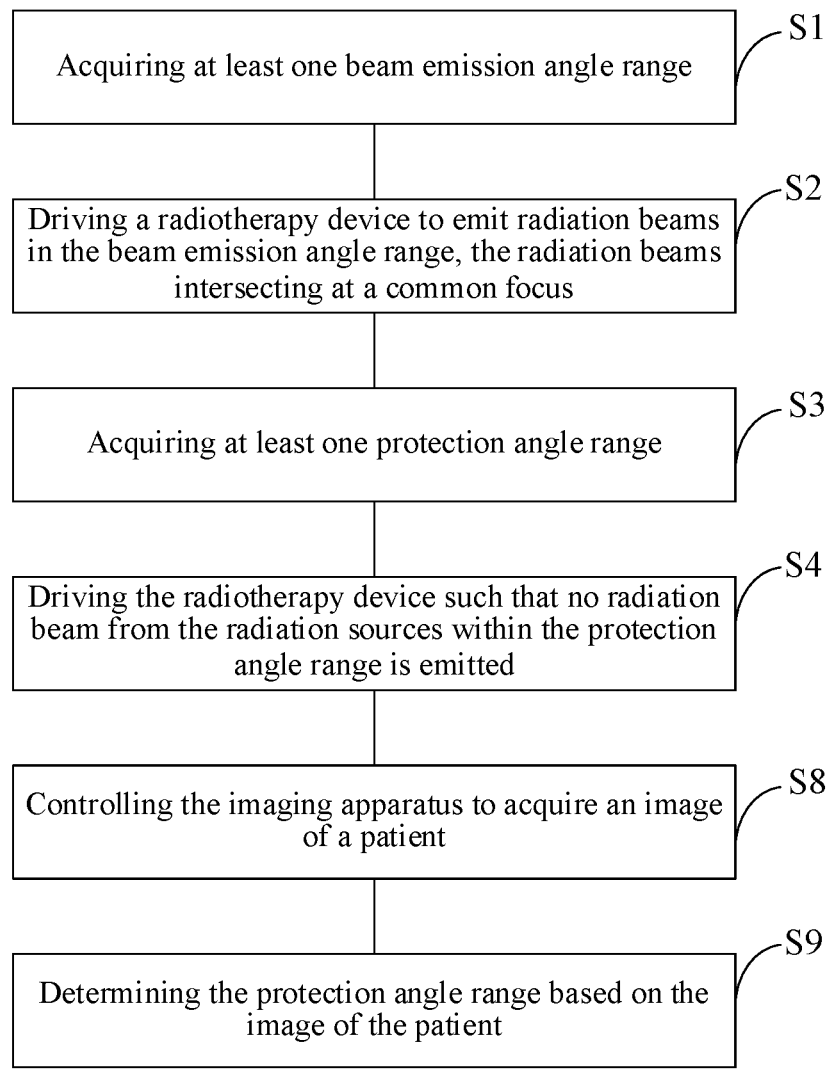
FIG. 20 is a schematic diagram of yet still another control driving method provided in an embodiment of the present disclosure.

For example, the radiotherapy device as shown in FIG. 7, FIG. 10, and FIG. 11 further includes an imaging apparatus, and the common focus is located within an imaging region of the imaging apparatus. As shown in FIG. 20, the control driving method further includes:

Step S8: controlling the imaging apparatus to acquire an image of a patient.

Step S9: determining the protection angle range based on the image of the patient.

Likewise, the protection angle range in step S3 may be a protection angle range determined by the therapist based on the image of the patient before radiotherapy, and may be determined or adjusted based on the acquired image during treatment.

It should be noted that, for the control driving method provided in the present disclosure, the sequence of the above steps is not limited in the present disclosure, and only an example description is provided with the figures as an example in the present disclosure.

The following is a control driving device corresponding to the control driving method for the radiotherapy device provided in the present disclosure. The control driving method may be referred to for a part of description of the driving apparatus. The description will not be repeated below.

In a control driving device of the radiotherapy device provided in the present disclosure, the radiotherapy device includes a plurality of radiation sources, and source points of the plurality of radiation sources are within a preset included angle range in a longitude direction. The control driving device includes a processor configured to acquire at least one beam emission angle range; and drive the radiotherapy device to emit radiation beams in the beam emission angle range, the radiation beams intersecting at a common focus.

In the control driving device provided in the present disclosure, the processor is further configured to acquire at least one protection angle range; and drive the radiotherapy device such that no radiation beam from the radiation sources within the protection angle range is emitted.

In the control driving device provided in the present disclosure, the processor is further configured to acquire a plurality of beam emission angle ranges, and the radiotherapy device operates at different speeds within at least two of the beam emission angle ranges.

In the control driving device provided in the present disclosure, the processor is further configured to drive the radiotherapy device to reciprocate within the beam emission angle range.

In the control driving device provided in the present disclosure, the radiation sources are γ-radioactive sources, the radiotherapy device includes a source carrier and a collimator, the source carrier is provided with a plurality of γ-radioactive sources, the plurality of γ-radioactive sources are distributed within the preset included angle range in the longitude direction, the collimator is provided with a plurality of collimating hole groups, each of the collimating hole groups is distributed within the preset included angle range in the longitude direction; and the processor is configured to drive the radiotherapy device such that radiation beams emitted from the plurality of γ-radioactive sources are emitted after passing through collimating holes of the collimator.

In the control driving device provided in the present disclosure, the radiation sources are γ-radioactive sources, the radiotherapy device includes a source carrier and a collimator, the source carrier is provided with a plurality of γ-radioactive sources, the plurality of γ-radioactive sources are distributed within the preset included angle range in the longitude direction, the collimator is provided with a plurality of collimating hole groups, each of the collimating hole groups is distributed within the preset included angle range in the longitude direction; and the processor is configured to drive the radiotherapy device such that the radiation beams emitted from the plurality of γ-radioactive sources are shielded by the collimator.

In the control driving device provided in the present disclosure, the radiotherapy device further includes a source switch body, and the processor is further configured to drive the radiotherapy device such that the radiation beams emitted from the plurality of γ-radioactive sources are shielded by the source switch body.

In the control driving device provided in the present disclosure, the radiotherapy device further includes a switch body, the switch body is located between the source carrier and the collimator, and the switch body is provided with at least two sets of hole sites corresponding to the γ-radioactive sources, where one set of hole sites are all through holes, and each of the rest sets of the hole sites includes through hole sites and shielding sites; and the processor is further configured to drive the switch body such that a part of the radiation beams emitted from the plurality of γ-radioactive sources are shielded by the shielding sites of the switch body.

In the control driving device provided in the present disclosure, a space between two adjacent collimating holes in a same collimating hole group is greater than a size of the γ-radioactive source in the longitude direction; and the processor is further configured to drive the radiotherapy device such that the plurality of γ-radioactive sources is misaligned with the collimating holes, where a part of the radiation beams emitted from the γ-radioactive sources are shielded by edge regions of the collimating hole group, and the rest of the radiation beams emitted from the γ-radioactive sources are shielded by a space region between the collimating holes.

In the control driving device provided in the present disclosure, the radiation beams are the X-ray beams, and the radiotherapy device includes one or a plurality of X-ray accelerating systems; and the processor is configured to drive the one X-ray accelerating system to emit a plurality of X-ray beams in a beam emission angle range; or drive the plurality of X-ray accelerating systems to emit a plurality of X-ray beams in the beam emission angle range.

In the control driving device provided in the present disclosure, the radiation beams are the X-ray beams, and the radiotherapy device includes one or a plurality of X-ray accelerating systems; and the processor is configured to switch off all or a part of X-ray beams from the one X-ray accelerating system; or switch off all or a part of the plurality of X-ray accelerating systems.

In the control driving device provided in the present disclosure, the radiotherapy device further includes an imaging apparatus, the common focus is located within an imaging region of the imaging apparatus; and the processor is further configured to control the imaging apparatus to acquire an image of a patient; and determine the beam emission angle range based on the image of the patient.

In the control driving device provided in the present disclosure, the radiotherapy device further includes an imaging apparatus, the common focus is located within an imaging region of the imaging apparatus; and the processor is further configured to control the imaging apparatus to acquire an image of a patient; and determine the protection angle range based on the image of the patient.

The present disclosure provides a radiotherapy system, including: the radiotherapy device provided in the present disclosure, and the control driving device provided in the present disclosure.

It should be noted that the term "and/or" in embodiments of the present disclosure is merely an association relationship describing associated objects, and means that there may be three relationships. For example, A and/or B may mean that A exists alone, both A and B exist, or B exists alone. In addition, the character "/" herein generally means that there is an "or" relationship between associated objects therebefore and thereafter.

The above description only provides alternative embodiments of the present disclosure, and is not intended to limit the present disclosure. Any modification, equivalent replacement, improvement, and the like made within the spirit and principles of the present disclosure should be included within the scope of protection of the present disclosure.

What is claimed is:

1. A radiotherapy device, comprising a radiation source apparatus, wherein the radiation source apparatus comprises a plurality of radiation sources, a source carrier and a collimator, source points of the plurality of radiation sources are within a preset included angle range in a longitude direction, the collimator is provided with a plurality of collimating hole groups, and an included angle of each of the collimating hole groups in the longitude direction is within the preset included angle range, wherein the preset included angle range is 5 to 60 degrees; and each of the collimating hole groups comprises a plurality of collimating holes, and radiation beams emitted from the plurality of radiation sources intersect at a common focus after passing through the collimating holes of the collimating hole groups, wherein the source carrier comprises a source box and a source box region conforming to a shape of the source box, the source box is detachably fixed at the source box region, the plurality of radiation sources are mounted in the source box, the source box is provided with a first connecting part, the source carrier is provided with a second connecting part, and the first connecting part is configured to connect the second connecting part.

2. The radiotherapy device according to claim 1, wherein the radiation sources are γ-radioactive source.

3. The radiotherapy device according to claim 1, wherein the collimator further comprises a shielding site configured to shield the radiation beams of the plurality of radiation sources, the plurality of collimating hole groups comprise a first collimating hole group, a second collimating hole group, a third collimating hole group and a fourth collimating hole group, which are successively arranged in the longitude direction, the shielding site is between the second and third collimating hole group, wherein the collimator is provided with a shielding body at the shielding site, and a material density of the shielding body is greater than a material density of the collimator.

4. The radiotherapy device according to claim 1, wherein a space between two adjacent collimating holes in a same collimating hole group is greater than a size of the radiation source in the longitude direction.

5. The radiotherapy device according to claim 1, wherein the plurality of radiation sources have different latitudes.

6. The radiotherapy device according to claim 1, wherein the collimator comprises an inner collimator and an outer collimator, which are relatively rotatable, collimating holes of the inner collimator are taper holes, and collimating holes of the outer collimator are straight holes.

7. The radiotherapy device according to claim 1, wherein the radiation source apparatus has a center axis and an end surface perpendicular to the center axis, the plurality of radiation sources are configured to rotate around the center axis, the common focus is on the center axis, the plurality of radiation sources are on a first side of the end surface, and the common focus is on a second side of the end surface.

8. The radiotherapy device according to claim 7, further comprising an imaging apparatus on the second side of the end surface, wherein the imaging apparatus is configured to rotate around the center axis.

9. The radiotherapy device according to claim 7, further comprising a shielding block provided on the second side of the end surface, wherein the shielding block is configured to rotate around the center axis so to follow the rotation of the plurality of radiation sources, and the radiation beams emitted from the plurality of radiation sources are shielded by the shielding block after passing through the common focus.

10. A control driving method for a radiotherapy device, the radiotherapy device comprising a plurality of radiation sources and a source carrier, source points of the plurality of radiation sources being within a preset included angle range in a longitude direction, the source carrier comprises a source box and a source box region conforming to a shape of the source box, the source box is detachably fixed at the source box region, the plurality of radiation sources are mounted in the source box, the source box is provided with a first connecting part, the source carrier is provided with a second connecting part, and the first connecting part is configured to connect the second connecting part, the method comprising:
  acquiring at least one beam emission angle range; and
  driving the radiotherapy device to emit radiation beams in the beam emission angle range, the radiation beams intersecting at a common focus.

11. The control driving method according to claim 10, wherein the radiation sources are γ-radioactive sources, the radiotherapy device further comprises a collimator, the collimator is provided with a plurality of collimating hole groups, and each of the collimating hole groups is distributed within the preset included angle range in the longitude direction; and
  the driving the radiotherapy device to emit radiation beams in the beam emission angle range comprises: driving the radiotherapy device such that radiation beams emitted from the plurality of γ-radioactive sources are emitted after passing through collimating holes of the collimator.

12. The control driving method according to claim 10, wherein the radiation sources are γ-radioactive sources, the radiotherapy device further comprises a collimator, the collimator is provided with a plurality of collimating hole groups, and each of the collimating hole groups is distributed within the preset included angle range in the longitude direction; and
  the driving the radiotherapy device such that no radiation beam from the radiation sources within a protection angle range is emitted specifically comprises: driving the radiotherapy device such that the radiation beams emitted from the plurality of γ-radioactive sources are shielded by the collimator.

13. The control driving method according to claim 12, wherein the radiotherapy device further comprises a source switch body, and the driving the radiotherapy device such that no radiation beam from the radiation sources within the protection angle range is emitted comprises: driving the radiotherapy device such that the radiation beams emitted from the plurality of γ-radioactive sources are shielded by the source switch body.

14. The control driving method according to claim 13, wherein the source switch body is provided on the collimator.

15. The control driving method according to claim 12, wherein a space between two adjacent collimating holes in a same collimating hole group is greater than a size of the γ-radioactive source in the longitude direction; and
  the driving the radiotherapy device such that no radiation beam from the radiation sources within the protection angle range is emitted comprises: driving the radiotherapy device such that the plurality of γ-radioactive sources is misaligned with the collimating holes, wherein a part of the radiation beams emitted from the γ-radioactive sources are shielded by edge regions of the collimating hole group, and the rest of the radiation beams emitted from the γ-radioactive sources are shielded by a space region between the collimating holes.

16. The control driving method according to claim 10, wherein the radiation beams are the X-ray beams, and the radiotherapy device comprises one or a plurality of X-ray accelerating systems; and
  the driving the radiotherapy device to emit radiation beams in the beam emission angle range specifically comprises: driving the one X-ray accelerating system to emit a plurality of X-ray beams in the beam emission angle range; or driving the plurality of X-ray accelerating systems to emit a plurality of X-ray beams in the beam emission angle range.

17. The control driving method according to claim 12, wherein the radiation beams are the X-ray beams, and the radiotherapy device comprises one or a plurality of X-ray accelerating systems; and
  the driving the radiotherapy device such that no radiation beam from the radiation sources within a protection angle range is emitted comprises:
  switching off all or a part of X-ray beams from the one X-ray accelerating system; or switching off all or a part of the plurality of X-ray accelerating systems.

18. The control driving method according to claim 10, wherein the common focus is located outside an end surface of the radiation source apparatus.

19. The control driving method according to claim 18, wherein the radiotherapy device further comprises an imaging apparatus, and the common focus is located within an imaging region of the imaging apparatus; the method further comprising:
  controlling the imaging apparatus to acquire an image of a patient; and
  determining the beam emission angle range based on the image of the patient.

20. The control driving method according to claim 18, wherein the radiotherapy device further comprises an imaging apparatus, and the common focus is located within an imaging region of the imaging apparatus; the method further comprising:
  controlling the imaging apparatus to acquire an image of a patient; and
  determining a protection angle range based on the image of the patient.

* * * * *